US009927383B2

United States Patent
Roh et al.

(10) Patent No.: US 9,927,383 B2
(45) Date of Patent: Mar. 27, 2018

(54) APPARATUS AND METHOD FOR PREVENTING MALFUNCTION IN AN ELECTRONIC DEVICE

(71) Applicant: Samsung Electronics Co., Ltd., Gyeonggi-do (KR)

(72) Inventors: Hyun-Jong Roh, Gyeonggi-do (KR); Min-Woo Oh, Gyeonggi-do (KR); Jin-Hee Won, Gyeonggi-do (KR); Dong-Yup Lee, Gyeonggi-do (KR); Ho-Chul Hwang, Seoul (KR)

(73) Assignee: Samsung Electronics Co., Ltd (KR)

( * ) Notice: Subject to any disclaimer, the term of this patent is extended or adjusted under 35 U.S.C. 154(b) by 136 days.

(21) Appl. No.: 14/753,852

(22) Filed: Jun. 29, 2015

(65) Prior Publication Data

US 2015/0377810 A1    Dec. 31, 2015

(30) Foreign Application Priority Data

Jun. 27, 2014    (KR) ........................ 10-2014-0079977

(51) Int. Cl.
*G01R 27/08*    (2006.01)
*G01N 27/04*    (2006.01)
*G01N 27/62*    (2006.01)
*G01L 21/30*    (2006.01)
*H04R 5/04*    (2006.01)
*G01N 27/64*    (2006.01)
*H01R 24/58*    (2011.01)

(52) U.S. Cl.
CPC ............ *G01N 27/048* (2013.01); *G01L 21/30* (2013.01); *G01N 27/62* (2013.01); *H04R 5/04* (2013.01); *G01N 27/64* (2013.01); *H01R 24/58* (2013.01); *H04R 2420/05* (2013.01)

(58) Field of Classification Search
CPC .... G01N 27/048; G01N 17/00; G01N 17/006; G01N 17/02; G01N 27/62; G01N 27/64; G01L 21/30; H01J 41/00; H01J 41/02
USPC .......... 324/76.11–76.83, 459, 600, 649, 691, 324/693, 694
See application file for complete search history.

(56) References Cited

U.S. PATENT DOCUMENTS

| 6,069,960 A | 5/2000 | Mizukami et al. |
| 6,573,746 B2 | 6/2003 | Kim et al. |
| 2003/0153205 A1 | 8/2003 | Corey et al. |

(Continued)

FOREIGN PATENT DOCUMENTS

| KR | 1020020042093 | 6/2002 |
| KR | 1020040026759 | 4/2004 |

OTHER PUBLICATIONS

European Search Report dated Oct. 16, 2015 issued in counterpart application No. 15174060.2-1901, 7 pages.

(Continued)

*Primary Examiner* — Huy Q Phan
*Assistant Examiner* — Raul Rios Russo
(74) *Attorney, Agent, or Firm* — The Farrell Law Firm, P.C.

(57) ABSTRACT

A method for operation of an electronic device and an electronic device are provided. The method includes determining if an object is detected at a first terminal and a second terminal among a plurality of terminals of an ear jack. If the object is detected, the impedance of the second terminal is calculated, and a type of the object is determined according to the calculated impedance.

20 Claims, 10 Drawing Sheets

(56) References Cited

U.S. PATENT DOCUMENTS

| | | | | |
|---|---|---|---|---|
| 2006/0094458 | A1* | 5/2006 | Kitaji | H04B 1/0458 455/522 |
| 2008/0139042 | A1 | 6/2008 | Liang | |
| 2009/0296952 | A1 | 12/2009 | Pantfoerder et al. | |
| 2010/0303251 | A1* | 12/2010 | Im | H04R 1/1041 381/74 |
| 2011/0099298 | A1* | 4/2011 | Chadbourne | G06F 11/3051 710/10 |
| 2011/0161050 | A1 | 6/2011 | Montena et al. | |
| 2011/0296358 | A1 | 12/2011 | Dewey, III et al. | |
| 2012/0051554 | A1* | 3/2012 | Modi | H04R 5/04 381/74 |
| 2013/0020882 | A1 | 1/2013 | Prentice | |
| 2013/0293240 | A1 | 11/2013 | Seo et al. | |
| 2014/0038460 | A1 | 2/2014 | Lee et al. | |
| 2014/0064503 | A1* | 3/2014 | Ko | H04R 29/001 381/59 |
| 2014/0191874 | A1* | 7/2014 | Stevens | H03K 17/94 340/604 |
| 2014/0233741 | A1* | 8/2014 | Gustavsson | H04R 5/04 381/58 |
| 2015/0326970 | A1* | 11/2015 | Miske | H04R 1/1041 381/123 |
| 2015/0358719 | A1* | 12/2015 | Mackay | G06F 11/3051 381/384 |

OTHER PUBLICATIONS

International Search Report dated Nov. 17, 2015 issued in counterpart application No. PCT/KR2015/006595, 10 pages.

* cited by examiner

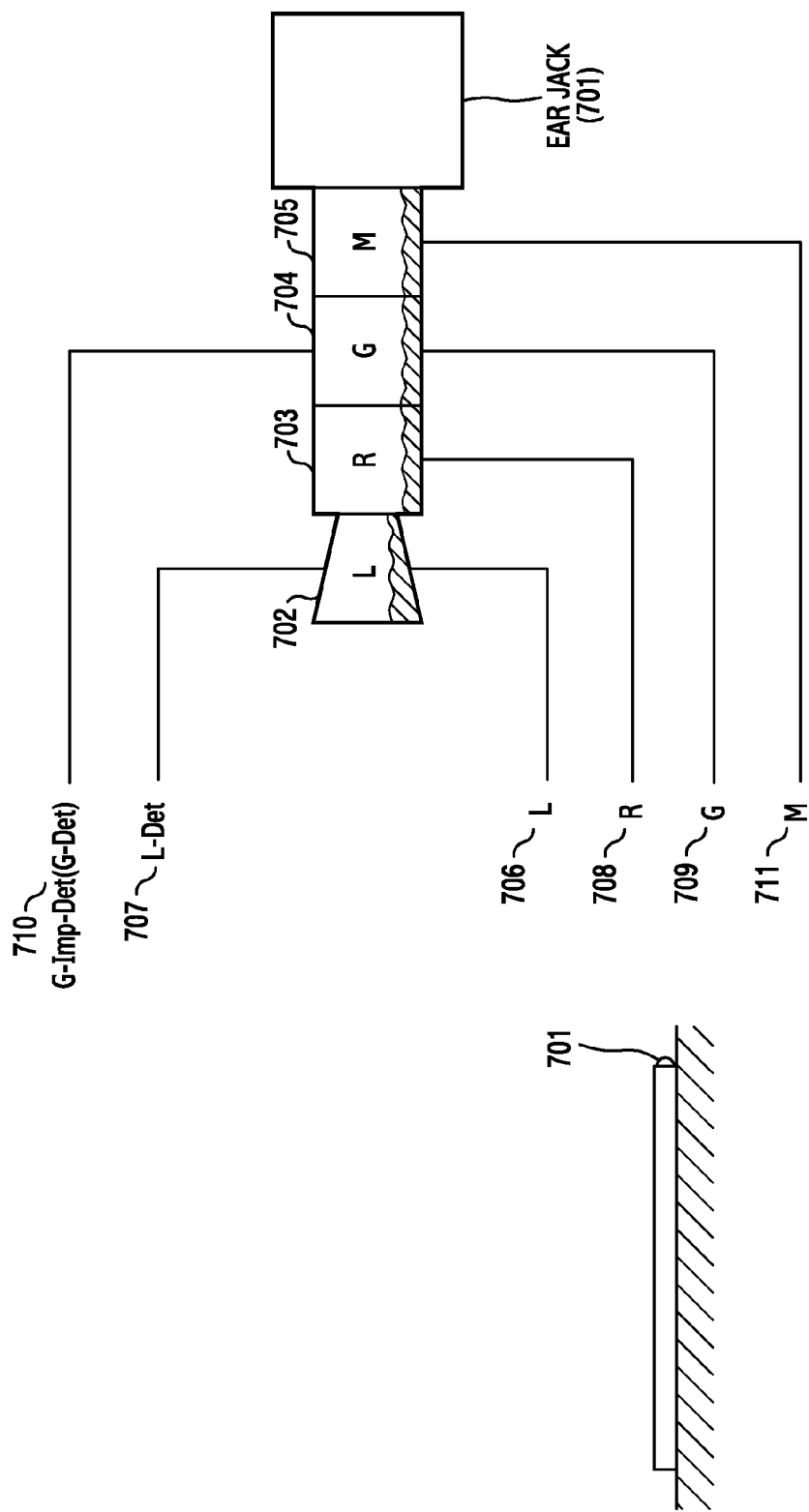

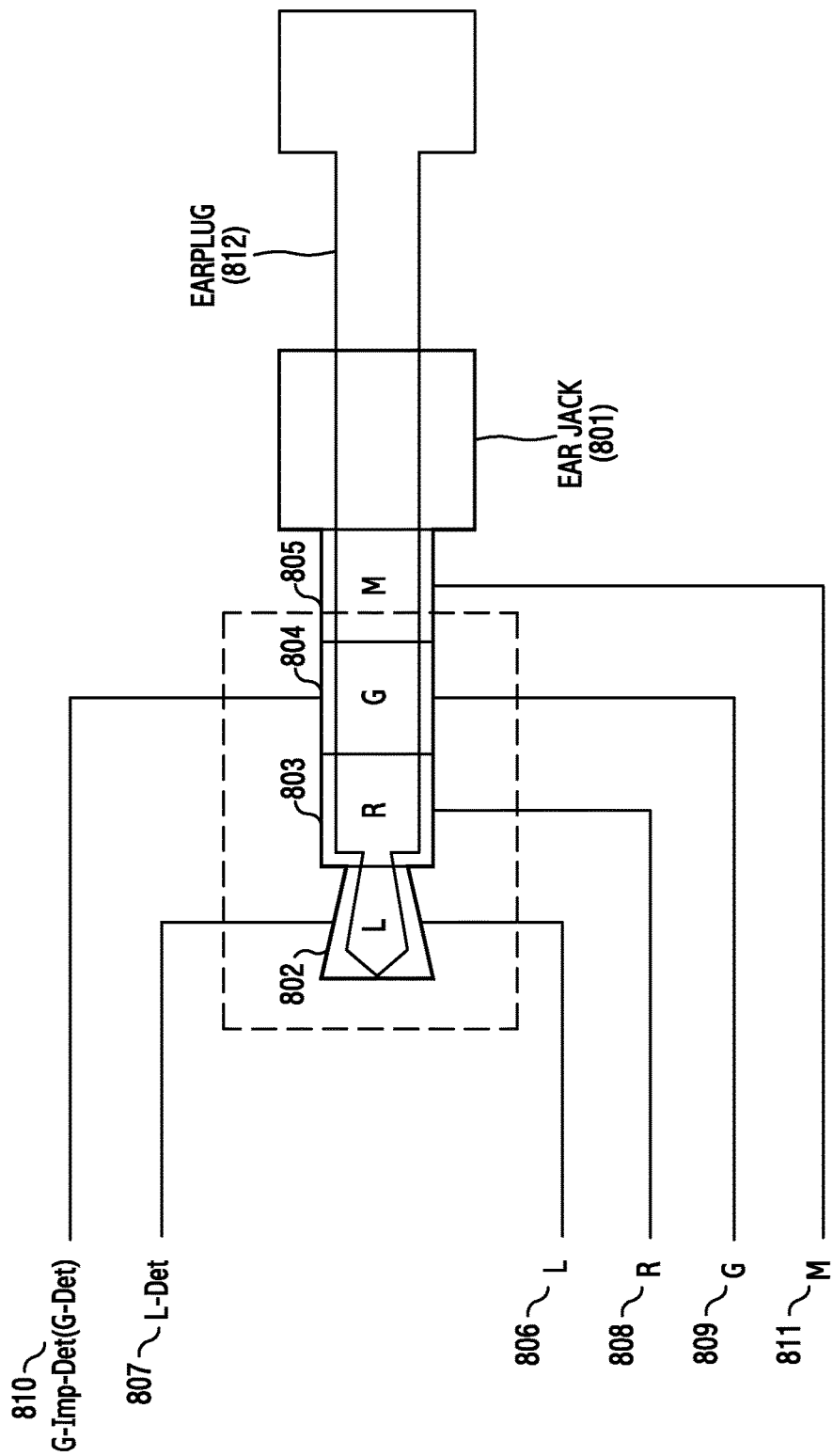

APPARATUS AND METHOD FOR PREVENTING MALFUNCTION IN AN ELECTRONIC DEVICE

PRIORITY

This application claims priority under 35 U.S.C. § 119(a) to a Korean Patent Application filed in the Korean Intellectual Property Office on Jun. 27, 2014 and assigned Serial No. 10-2014-0079977, the contents of which are incorporated herein by reference.

BACKGROUND

1. Field of the Invention

Various embodiments of the present invention relate to an apparatus and method for preventing malfunction in an electronic device.

2. Description of the Related Art

With the growth of their functions, electronic devices are now able to perform various functions via ear jacks into which earplugs can be inserted.

For example, an electronic device will output sound via an earplug, or can recognize sound introduced from the earplug, when sensing that the earplug has been inserted into the ear jack.

According to existing technologies, introduction of moisture into an ear jack of an electronic device can cause the electronic device to incorrectly convert into an earphone mode by wrongly recognizing that an earplug is inserted into the ear jack.

SUMMARY OF THE INVENTION

The present invention has been made to address at least the above problems and disadvantages, and to provide at least the advantages below.

Accordingly, an aspect of the present invention provides an apparatus and method capable of, when an object is sensed at a first terminal of an ear jack and a second terminal thereof, determining the impedance of the second terminal and determining whether an earplug is inserted into the ear jack, thereby preventing malfunction of the ear jack caused by the introduction of moisture.

Another aspect of the present invention provides an apparatus and method for, only when an object is sensed at a first terminal of an ear jack and a second terminal thereof, operating a circuit for determining the impedance of the second terminal, thereby preventing unnecessary power consumption.

According to an aspect of the present invention, an operation method of an electronic device is provided that includes determining if an object is detected at a first terminal and a second terminal among terminals of an ear jack. If the object is detected, the impedance of the second terminal is calculated, and a type of object is determined according to the calculated impedance.

According to another aspect of the present invention, an electronic device is provided that includes a jack detector configured to determine if an object is detected at a first terminal and a second terminal among terminals of an ear jack, an impedance detector configured to determine, if the object is detected, the impedance of the second terminal, and a processor configured to determine a type of the object according to the calculated impedance.

BRIEF DESCRIPTION OF THE DRAWINGS

The above and other aspects, features and advantages of the present invention will become more apparent from the following detailed description when taken in conjunction with the accompanying drawings in which:

FIGS. 7A and 7B illustrate another embodiment of an electronic device when an object is sensed at an ear jack according to an embodiment of the present invention;

FIG. 8 illustrates a further embodiment of an electronic device when an object is sensed at an ear jack according to an embodiment of the present invention;

DETAILED DESCRIPTION OF EMBODIMENTS OF THE PRESENT INVENTION

Figure 1:
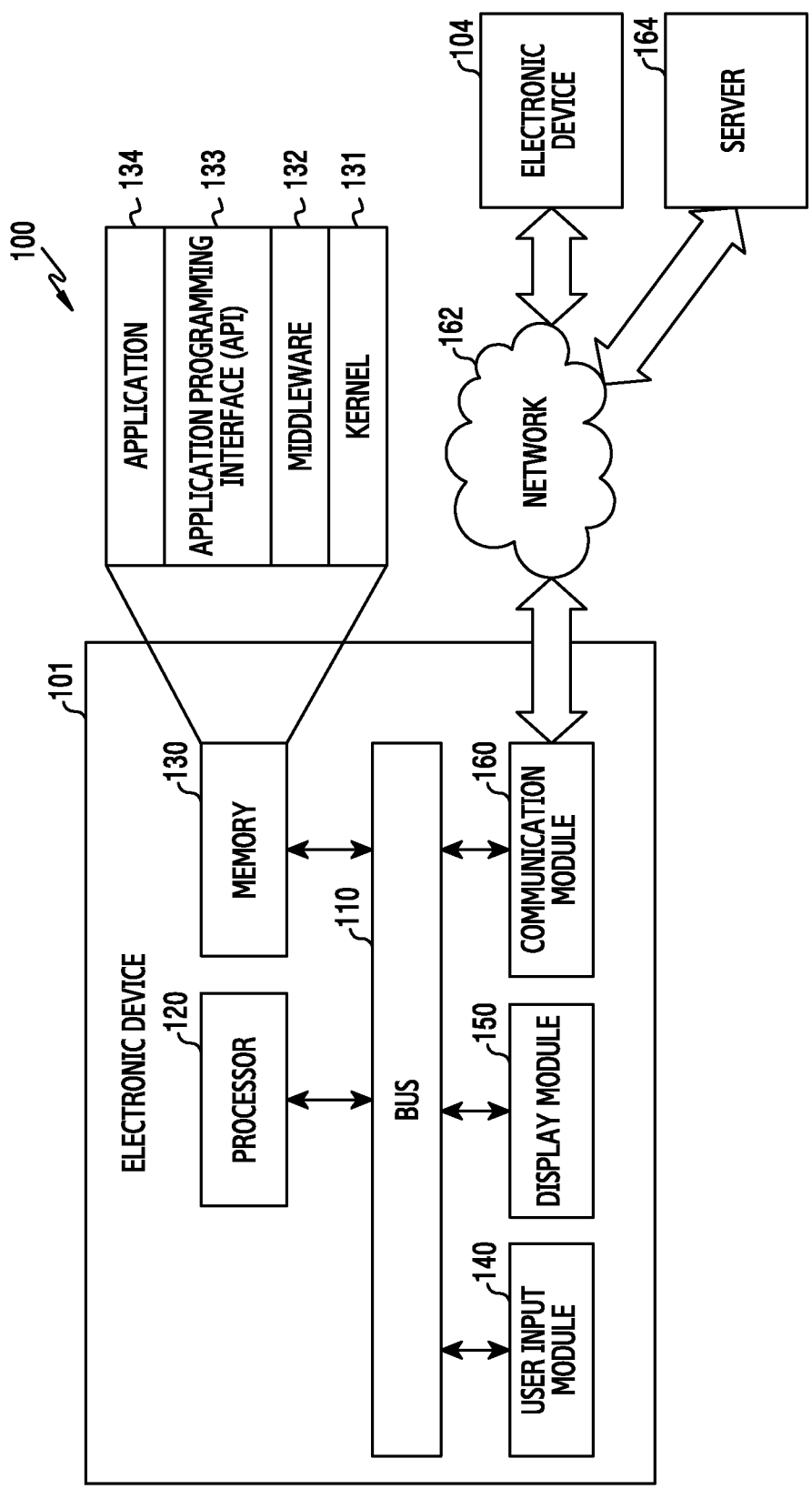
FIG. 1 illustrates a network environment including an electronic device according to an embodiment of the present invention.

The following description with reference to the accompanying drawings is provided to assist in a comprehensive understanding of various embodiments of the present invention as defined by the claims and their equivalents. The description includes various specific details to assist in that understanding but these are to be regarded as mere examples. Accordingly, those of ordinary skill in the art will recognize that various changes and modifications of the various embodiments described herein can be made without departing from the scope and spirit of the present invention. In addition, descriptions of well-known functions and constructions may be omitted for clarity and conciseness.

The terms and words used in the following description and claims are not limited to their dictionary meanings, but are merely used to enable a clear and consistent understanding of the present disclosure. Accordingly, it should be apparent to those skilled in the art that the following description of various embodiments of the present invention is provided for illustration purposes only and not for the purpose of limiting the present invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

As used in various embodiments of the present invention, the expressions "include", "may include" and other conjugates refer to the existence of a corresponding disclosed function, operation, or constituent element, and do not limit one or more additional functions, operations, or constituent elements. Further, the terms "include", "have" and their conjugates may be construed to denote a certain characteristic, number, operation, constituent element, component or a combination thereof, but may not be construed to exclude the existence of or a possibility of addition of one or more other characteristics, numbers, operations, constituent elements, components or combinations thereof.

Further, the expression "or" includes any or all combinations of words enumerated together. For example, the expression "A or B" may include A, may include B, or may include both A and B.

The expressions "first, "second", and the like may modify various elements in the present disclosure, but do not limit the sequence and/or importance of corresponding elements. The above expressions may be used merely for the purpose of distinguishing one element from the other elements.

When an element is referred to as being "coupled" or "connected" to any other element, it should be understood that not only the element may be coupled or connected directly to the other element, but also a third element may be interposed therebetween. Contrarily, when an element is referred to as being "directly coupled" or "directly connected" to any other element, it should be understood that no element is interposed therebetween.

The terms as used herein are merely for the purpose of describing particular embodiments and are not intended to limit the present invention. Further, all the terms used herein, including technical terms and scientific terms, should be interpreted to have the same meanings as commonly understood by those skilled in the art to which the present disclosure pertains, and should not be interpreted to have ideal or excessively formal meanings unless explicitly defined in various embodiments of the present disclosure.

An electronic device according to various embodiments of the present invention may be a device including a communication function. The electronic device may, for example, include at least one of a smart phone, a tablet personal computer (PC), a mobile phone, a video phone, an e-book reader, a desktop PC, a laptop PC, a netbook computer, a personal digital assistant (PDA), a portable multimedia player (PMP), an MP3 player, a mobile medical device, a camera, a wearable device, e.g., a head-mounted-display (HMD) such as electronic glasses, electronic clothing, an electronic bracelet, an electronic necklace, an electronic appcessory, an electronic tattoo, or a smart watch, a television (TV), a digital video disc (DVD) player, an audio, a refrigerator, an air conditioner, a vacuum cleaner, an oven, a microwave oven, a washing machine, an air cleaner, a set-top box, a TV box, e.g., Samsung HomeSync™, Apple TV™, or Google TV™, a game console, an artificial intelligence robot, an electronic dictionary, an electronic key, a camcorder, medical equipment, e.g., a magnetic resonance angiography (MRA) machine, a magnetic resonance imaging (MRI) machine, a computed tomography (CT) scanner, or an ultrasonic machine, a navigation device, a global positioning system (GPS) receiver, an event data recorder (EDR), a flight data recorder (FDR), a vehicle infotainment device, electronic equipment for a ship, e.g., ship navigation equipment and a gyrocompass, avionics, security equipment, an industrial or home robot, a part of furniture or building/structure, an electronic board, an electronic signature receiving device, a projector, and various measuring instruments, e.g., a water meter, an electricity meter, a gas meter, or a wave meter, each of which includes a communication function. The electronic device may be a combination of one or more of the aforementioned various devices. Further, it will be apparent to those skilled in the art that the electronic device according to various embodiments of the present invention is not limited to the aforementioned devices.

Hereinafter, an electronic device and method of operation of thereof according to the various embodiments of the present invention will be described with reference to the accompanying drawings. As used herein, the term "user" may indicate a person using an electronic device or a device, e.g. an artificial intelligence electronic device, using an electronic device.

FIG. 1 illustrates a network environment 100 including an electronic device 101.

Referring to FIG. 1, a network environment 100 includes an electronic device 101. The electronic device 101 includes a bus 110, a processor 120, a memory 130, an Input/Output (I/O) interface 140, a display 150, a communication interface 160, and/or the like.

The bus 110 provides circuitry that connects the foregoing components and allows communication between the foregoing components. For example, the bus 110 connects components of the electronic device 101 so as to allow control messages and/or other information to be communicated between the connected components.

The processor 120 may, e.g., receive instructions from other components, e.g., the memory 130, the I/O interface 140, the display 150, the communication interface 160, and/or the like, interpret the received instructions, and execute computation or data processing according to the interpreted instructions.

The memory 130 may, e.g., store instructions and/or data that are received from, and/or generated by, other components, e.g., the memory 130, the I/O interface 140, the display 150, the communication interface 160, and/or the like. For example, the memory 130 includes programming modules such as a kernel 131, a middleware 132, an Application Programming Interface (API) 133, an application 134, and/or the like. Each of the foregoing programming modules may include a combination of at least two of software, firmware, or hardware.

The kernel 131 controls or manages system resources, e.g., the bus 110, the processor 120, the memory 130, and/or the like, used in executing operations or functions implemented in other programming modules such as, e.g., the middleware 132, the API 133, the application 134, and/or the like. The kernel 131 may provide an interface for allowing or otherwise facilitating the middleware 132, the API 133, the application 134, and/or the like, to access individual components of electronic device 101.

The middleware 132 provides a medium through which the kernel 131 may communicate with the API 133, the application 134, and/or the like to send and receive data. The middleware 132 may control, e.g., perform scheduling, load balancing, and/or the like, work requests by the application 134. For example, the middleware 132 may control work requests by the application 134 by assigning priorities for using system resources, e.g., the bus 110, the processor 120, the memory 130, and/or the like, of electronic device 101 to the application 134.

The API 133 provides an interface to control functions that the application 134 may provide at the kernel 131, the middleware 132, and/or the like. For example, the API 133 includes at least an interface or a function, e.g., command, for file control, window control, video processing, character control, and/or the like.

According to various embodiments of the present invention, the application 134 may include a short message service (SMS) application, a multimedia messaging service (MMS) application, an email application, a calendar application, an alarm application, a health care application, e.g., an exercise amount application, a blood sugar level measuring application, and/or the like, an environmental information application, e.g., an application that may provide atmospheric pressure, humidity, temperature information, and/or the like, an instant messaging application, a call application, an Internet browsing application, a gaming application, a media playback application, an image/video capture application, a file management application, and/or the like. In addition to or as an alternative to, the application 134 may be an application that is associated with information exchange between the electronic device 101 and an external electronic device, e.g., electronic device 104. As an example, the application 134 that is associated with the information exchange may include a notification relay application that may provide the external electronic device with a certain type of information, a device management application that may manage the external electronic device, and/or the like.

As an example, the notification relay application includes a functionality that provides notification generated by other applications at electronic device 101, e.g., the SMS/MMS application, the email application, the health care application, the environmental information application, the instant messaging application, the call application, the Internet browsing application, the gaming application, the media playback application, the image/video capture application, the file management application, and/or the like, to an external electronic device, e.g., the electronic device 104. In addition to or as an alternative to, the notification relay application may provide or receive notification from external electronic device 104, and may provide the notification to a user.

As an example, the device management application manages enabling or disabling of functions associated with least a portion of an external electronic device, e.g., the external electronic device itself, or one or more components of the external electronic device, in communication with electronic device 101, controlling of brightness or resolution of a display of the external electronic device, an application operated at, or a service (e.g., a voice call service, a messaging service, and/or the like) provided by, the external electronic device, and/or the like.

According to various embodiments of the present invention, as an example, the application 134 includes one or more applications that are determined according to a property, e.g., type of electronic device, and/or the like, of the external electronic device 104. For example, if the external electronic device is an mp3 player, the application 134 may include one or more applications related to music playback. As another example, if the external electronic device is a mobile medical device, the application 134 may be a health care-related application. According to various embodiments of the present invention, the application 134 may include at least one of an application that is preloaded at the electronic device 101, and an application that is received from the electronic device 104, and a server 164.

The I/O interface 140, for example, receives instruction and/or data from a user. The I/O interface 140 sends the instruction and/or the data, via the bus 110, to the processor 120, the memory 130, the communication interface 160, and/or the like. For example, the I/O interface 140 provides data associated with user input received via a touch screen to the processor 120. The I/O interface 140 outputs instructions and/or data received via the bus 110 from the processor 120, the memory 130, the communication interface 160, and/or the like, via an I/O device, e.g., a speaker, a display, and/or the like. For example, the I/O interface 140 outputs voice data, e.g., data processed using the processor 120, via a speaker.

The display 150 displays various types of information, e.g., multimedia, text data, and/or the like, to the user. As an example, the display 150 displays a graphical user interface (GUI) with which a user may interact with the electronic device 101.

The communication interface 160 facilitates communication between the electronic device 101 and an external device, e.g., the external electronic device 104, or a server 164. For example, the communication interface 160 connects to a network 162 through wireless communication or wired communication, and communicates with an external device. The wireless communication may include at least one of, for example, Wi-Fi, Bluetooth (BT), near field communication (NFC), GPS and cellular communication, e.g., long term evolution (LTE), LTE-advanced (LTE-A), code division multiple access (CDMA), wideband CDMA (WCDMA), universal mobile telecommunications system (UMTS), wireless broadband (WiBro), global system for mobile communications (GSM), etc. The wired communication may include at least one of, e.g., a universal serial bus (USB), a high definition multimedia interface (HDMI), a recommended standard 232 (RS-232), and plain old telephone service (POTS).

According to an embodiment of the present invention, the network 162 may be a communication network. The telecommunication network includes at least one of a computer network, Internet, Internet of things, and a telephone network. According to an embodiment of the present invention, a protocol, e.g., a transport layer protocol, data link layer protocol, or a physical layer protocol, for communication between the electronic device 101 and the external device may be supported by at least one of the applications 134, the API 133, the middleware 132, the kernel 131, and the communication interface 160.

Figure 2:
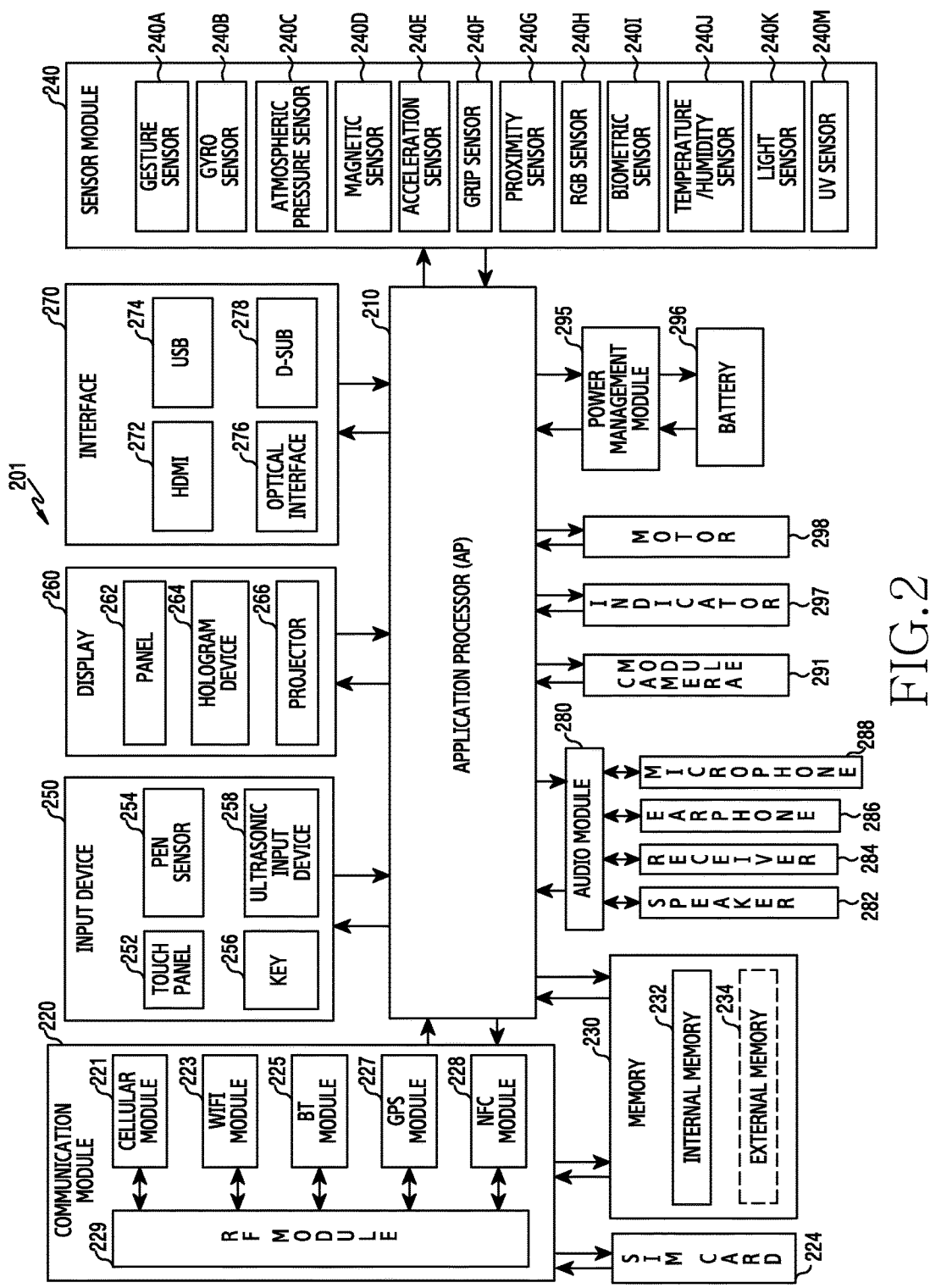
FIG. 2 illustrates an electronic device according to an embodiment of the present invention.

FIG. 2 illustrates an electronic device 201 according to aspects of the present invention.

The electronic device 201 includes, e.g., all or some of the components of the electronic device 101 illustrated in FIG. 1.

Referring to FIG. 2, the electronic device 201 includes at least one of an application processor (AP) 210, a communication module 220, a subscriber identifier module (SIM) card 224, a memory 230, a sensor module 240, an input device 250, a display 260, an interface 270, an audio module 280, a camera module 291, a power management module 295, a battery 296, an indicator 297, and a motor 298.

The AP 210 drives an operating system or an application program so as to control a plurality of hardware or software components connected to the AP, and processes various pieces of data including multimedia data and performs calculations. The AP 210 may be implemented by, for example, a system on chip (SoC). According to an embodiment of the present invention, the AP 210 may further include a graphic processing unit (GPU).

The communication module 220 may perform data transmission/reception in communication between the electronic device 101 and other electronic devices (for example, the external electronic device 102, the external electronic device 103, the external electronic device 104, or the server 164) through a network. According to an embodiment of the present invention, the communication module 220 includes a cellular module 221, a Wi-Fi module 223, a BT module 225, a GPS module 227, an NFC module 228, and a radio frequency (RF) module 229.

The cellular module 221 provides a voice, a call, a video call, a text message service, or an Internet service through a communication network (for example, LTE, LTE-A, CDMA, WCDMA, UMTS, WiBro, or GSM). Furthermore, the cellular module 221 distinguishes between and authenticates electronic devices within a communication network by using, for example, the SIM card 224. According to an embodiment of the present invention, the cellular module 221 performs at least some of the functions which the AP 210 may provide. For example, the cellular module 221 may perform at least some of the multimedia control functions.

According to an embodiment of the present invention, the cellular module 221 may include a communication processor (CP). Furthermore, the cellular module 221 may be implemented by, for example, an SoC. Although the components such as the cellular module 221, e.g., the CP, the memory 230, and the power management module 295 are illustrated as components separated from the AP 210 in FIG. 2, the AP 210 may include at least some of the aforementioned components, e.g., the cellular module 221, in an embodiment of the present invention.

According to an embodiment of the present invention, the AP 210 or the cellular module 221, e.g., the CP, loads a command or data received from at least one of a non-volatile memory and other components connected thereto into a volatile memory and processes the loaded command or data. Further, the AP 210 or the cellular module 221 stores data received from or generated by at least one of the other components in a non-volatile memory.

For example, each of the Wi-Fi module 223, the BT module 225, the GPS module 227, and the NFC module 228 includes a processor for processing data transmitted/received through the corresponding module. Although the cellular module 221, the Wi-Fi module 223, the BT module 225, the GPS module 227, and the NFC module 228 are illustrated as separate blocks in FIG. 2, at least some, e.g., two or more, of the cellular module 221, the Wi-Fi module 223, the BT module 225, the GPS module 227, and the NFC module 228 may be included in one IC or one IC package in an embodiment of the present invention. For example, at least some (for example, the CP corresponding to the cellular module 221 and the Wi-Fi processor corresponding to the Wi-Fi module 223) of the processors corresponding to the cellular module 221, the Wi-Fi module 223, the BT module 225, the GPS module 227, and the NFC module 228 may be implemented as one SoC.

The RF module 229 transmits/receives data via, e.g., RF signals. Although not illustrated, the RF module 229 may include, for example, a transceiver, a power amplifier module (PAM), a frequency filter, a low noise amplifier (LNA) or the like. Further, the RF module 229 may further include a component for transmitting/receiving electronic waves over a free air space in wireless communication, as well as over a conductor, a conducting wire or the like. Although the cellular module 221, the Wi-Fi module 223, the BT module 225, the GPS module 227, and the NFC module 228 share one RF module 229 in FIG. 2, at least one of the cellular module 221, the Wi-Fi module 223, the BT module 225, the GPS module 227, and the NFC module 228 may transmit/receive an RF signal through a separate RF module in one embodiment.

The SIM card 224 may be inserted into a slot formed in a predetermined portion of the electronic device. The SIM card 224 may include unique identification information (for example, an integrated circuit card identifier (ICCID)) or subscriber information (for example, an international mobile subscriber identity (IMSI)).

The memory 230 (for example, the memory 130) may include an internal memory 232 or an external memory 234. The internal memory 232 may include at least one of a volatile memory (for example, a dynamic random access memory (DRAM), a static RAM (SRAM), a synchronous dynamic RAM (SDRAM), or the like) or a non-volatile memory (for example, a one time programmable read only memory (OTPROM), a programmable ROM (PROM), an erasable and programmable ROM (EPROM), an electrically erasable and programmable ROM (EEPROM), a mask ROM, a flash ROM, a NAND flash memory, a NOR flash memory, or the like).

According to an embodiment of the present invention, the internal memory 232 may be a solid state drive (SSD). The external memory 234 may further include a flash drive, for example, a compact flash (CF), a secure digital (SD), a micro-SD, a mini-SD, an extreme digital (xD), a memory stick, or the like. The external memory 234 is functionally connected to the electronic device 201 through an interface. According to an embodiment of the present invention, the electronic device 201 may further include a storage device (or storage medium) such as a hard drive.

The sensor module 240 measures a physical quantity or senses an operation state of the electronic device 201, and converts the measured or sensed information into an electric signal. The sensor module 240 may include, for example, at least one of a gesture sensor 240A, a gyro sensor 240B, an atmospheric pressure sensor 240C, a magnetic sensor 240D, the acceleration sensor 240E, a grip sensor 240F, a proximity sensor 240G, a color sensor 240H (for example, red, green, and blue (RGB) sensor), a biometric sensor 240I, a temperature/humidity sensor 240J, an illumination sensor 240K, an Ultra Violet (UV) sensor 240M, and the geomagnetic sensor 240P. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris sensor, a fingerprint sensor, and the like. The sensor module 240 may further include a control circuit for controlling one or more sensors included therein.

The input device 250 may include a touch panel 252, a digital pen sensor 254, a key 256, or an ultrasonic input device 258. The touch panel 252 recognizes a touch input in at least one scheme among, for example, a capacitive type, a resistive type, an infrared type, and an acoustic wave type. The touch panel 252 may further include a control circuit. The capacitive type touch panel detects a physical contact or proximity. The touch panel 252 may further include a tactile layer. In this case, the touch panel 252 may provide a user with a tactile reaction.

The digital pen sensor 254 may be implemented by, for example, a method identical or similar to a method of receiving a touch input of a user, or a separate recognition method. The key 256 may include, for example, a physical button, an optical key, or a keypad. The ultrasonic input device 258 identifies data by detecting an acoustic wave with a microphone 288 of the electronic device 201 through an input unit generating an ultrasonic signal, and performs wireless detection. According to an embodiment of the present invention, the electronic device 201 may also receive a user input from an external device (for example, a computer or server) connected thereto using the communication module 220.

The display 260 (for example, the display 150) may include a panel 262, a hologram device 264, and/or a projector 266. For example, the panel 262 may be, for example, a liquid crystal display (LCD), an active matrix organic light emitting diode (AM-OLED), or the like. The panel 262 may be implemented to be, for example, flexible, transparent, or wearable. The panel 262 may be implemented by a single module together with the touch panel 252. The hologram device 264 may project a three dimensional image into the air by using an interference of light. The projector 266 may display an image by projecting light onto a screen. The screen may be internal or external to the electronic device 201. According to an embodiment of the present invention, the display 260 may further include a control circuit for controlling the panel 262, the hologram device 264, or the projector 266.

The interface 270 may include, for example, an HDMI 272, a USB 274, an optical interface 276, or a d-subminiature (D-sub) 278. The interface 270 may be included in, for example, the communication interface 160 illustrated in FIG. 1. Additionally or alternatively, the interface 270 may include, for example, a mobile high-definition Link (MHL) interface, an SD card/multi-media card (MMC) interface, or an Infrared data association (IrDA) standard interface.

The audio module 280 may bi-directionally convert a sound and an electrical signal. At least some components of the audio module 280 may be included in, for example, the input/output interface 140 illustrated in FIG. 1. The audio module 280 processes voice information input or output through, for example, a speaker 282, a receiver 284, earphones 286, or the microphone 288. The camera module 291 photographs still and moving images, and may include one or more image sensors (for example, a front sensor or a rear sensor), a lens, an image signal processor (ISP), or a flash (for example, an LED or a xenon lamp) according to an embodiment of the present invention.

The power management module 295 may manage power of the electronic device 201 and include, for example, a power management IC (PMIC), a charger IC, or a battery gauge. The PMIC may be mounted in, for example, an integrated circuit or an SoC semiconductor. Charging methods may be classified into a wired charging method and a wireless charging method. The charger IC may charge a battery and can prevent introduction of over-voltage or over-current from a charger.

According to an embodiment of the present invention, the charger IC may include a charger IC for at least one of the wired charging and the wireless charging. Examples of the wireless charging method may include a magnetic resonance type, a magnetic induction type, or an electromagnetic wave type, and an additional circuit for wireless charging, such as a coil loop circuit, a resonance circuit, or a rectifier circuit may be added.

The battery gauge measures, for example, a residual quantity of the battery 296, and a voltage, a current, or a temperature, such as during the charging. The battery 296 stores or generates electricity to supply power to the electronic device 201 using the stored or generated electricity. The battery 296 may include, for example, a rechargeable battery or a solar battery.

The indicator 297 displays a predetermined state of the electronic device 201 or a part of the electronic device 201, e.g., the AP 210, for example, a booting state, a message state, a charging state, or the like. The motor 298 converts an electrical signal into a mechanical vibration. Although not illustrated, the electronic device 201 may include a processing device (for example, a GPU) for supporting mobile TV. The processing device for supporting mobile TV processes, for example, media data associated with the standard of Digital Multimedia Broadcasting (DMB), Digital Video Broadcasting (DVB), a media flow, or the like.

Each of the above described elements of the electronic device according to various embodiments of the present invention may be formed of one or more components, and the name of a corresponding element may vary according to the type of an electronic device. The electronic device may be formed to include at least one of the above described components, and some of the components may be omitted or additional components may be further included. Further, some of the elements of the electronic device may be coupled to form a single entity while performing the same functions as those of the corresponding elements before the coupling.

Hereinafter, various embodiments in which the electronic device 101 performs a function corresponding to control information received by the electronic device 101 based on the received control information and displays the function on the display 150 of the electronic device 101 will be described.

Figure 3:
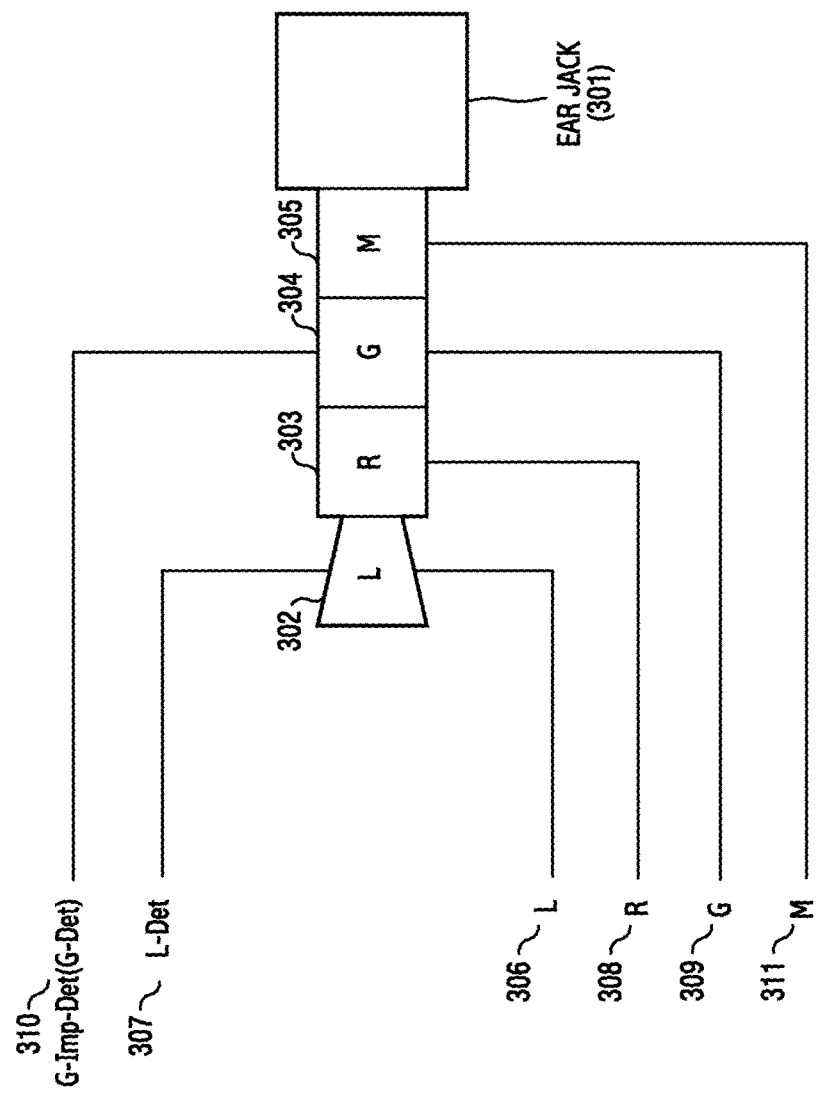
FIG. 3 illustrates a first embodiment of an ear jack according to an embodiment of the present invention.

FIG. 3 illustrates a first embodiment of an ear jack according to the present invention. According to various embodiments, an ear jack 301 provided in an electronic device includes a left (L) terminal 302, a right (R) terminal 303, a ground (G) terminal 304, and a microphone (M) terminal 305.

According to various embodiments, one side of the L terminal 302 is connected with a left (L) side 306. The left (L) side 306 outputs sound generated in the electronic device. The other side of the L terminal 302 is connected with a left-terminal detector (L-Det) 307. The left-terminal detector (L-Det) 307 detects if an object such as an earplug or moisture is in the ear jack 301. According to one embodiment, the L terminal 302 outputs sound, which is outputted from the L side 306, in the direction of the earplug, when the earplug is inserted into the ear jack 301.

According to various embodiments, the R terminal 303 is connected with a right (R) side 308. The right (R) side 308 outputs sound signals generated in the electronic device. According to one embodiment, the R terminal 303 may output sound signals, outputted from the R side 308, in the direction of the earplug, when the earplug is inserted into the ear jack 301.

According to various embodiments, one side of the G terminal 304 is connected with the ground 309. The other side of the G terminal 304 is connected with a G-terminal impedance detector/G-terminal jack detector (G-imp-Det/G-Det) 310. The G-terminal impedance detector/G-terminal jack detector (G-imp-Det/G-Det 310 detects if an object is sensed in the ear jack 301, and determines the impedance of the G terminal 304 when it is determined that the object sensed in the ear jack 301 is the earplug.

According to various embodiments, the M terminal 305 is connected with a microphone (M) side 311. The microphone (M) side 311 receives an input of sound when the earplug is inserted into the ear jack 301.

According to various embodiments, the L side 306 outputs sound generated in the electronic device, to the L terminal 302. According to one embodiment, the L side 306 receives a set predetermined electric current at a predetermined interval from the L-terminal detector (L-Det) 307.

According to various embodiments, the L-terminal detector (L-Det) 307 applies a set electric current in the direction of the L terminal 302, and detects if an object is sensed at the L terminal 302. According to one embodiment, by applying a set predetermined electric current at a predetermined interval in the direction of the L terminal 302 and sensing a variation of the impedance of the L terminal 302, the left-terminal detector (L-Det) 307 determines if the object is located at the L terminal 302.

According to various embodiments, the R side 308 outputs sound signals generated in the electronic device, to the R terminal 303.

According to various embodiments, the ground (G) 309 receives a set predetermined electric current from the G-terminal impedance detector/G-terminal jack detector (G-imp-Det/G-Det) 310.

According to various embodiments, the G-terminal impedance detector/G-terminal jack detector (G-imp-Det/G-Det) 310 detects if the object such as the earplug or moisture is sensed at the G terminal 304. According to one embodiment, by applying a set predetermined electric current at a predetermined interval in the direction of the G terminal 304 and sensing a variation of the impedance of the G terminal 304, the G-terminal impedance detector/G-terminal jack detector (G-imp-Det/G-Det) 310 determines if the object is located at the G terminal 304. According to one embodiment, upon sensing that the object is located at the G terminal 304, the G-terminal impedance detector/G-terminal jack detector (G-imp-Det/G-Det) 310 applies a set predetermined electric current (or voltage) in the direction of the G terminal 304, and determines the impedance of the G terminal 304.

According to various embodiments, the M side 311 is connected with the M terminal 305, and receives sound signals input when the earplug is inserted into the ear jack 301.

Figure 4:
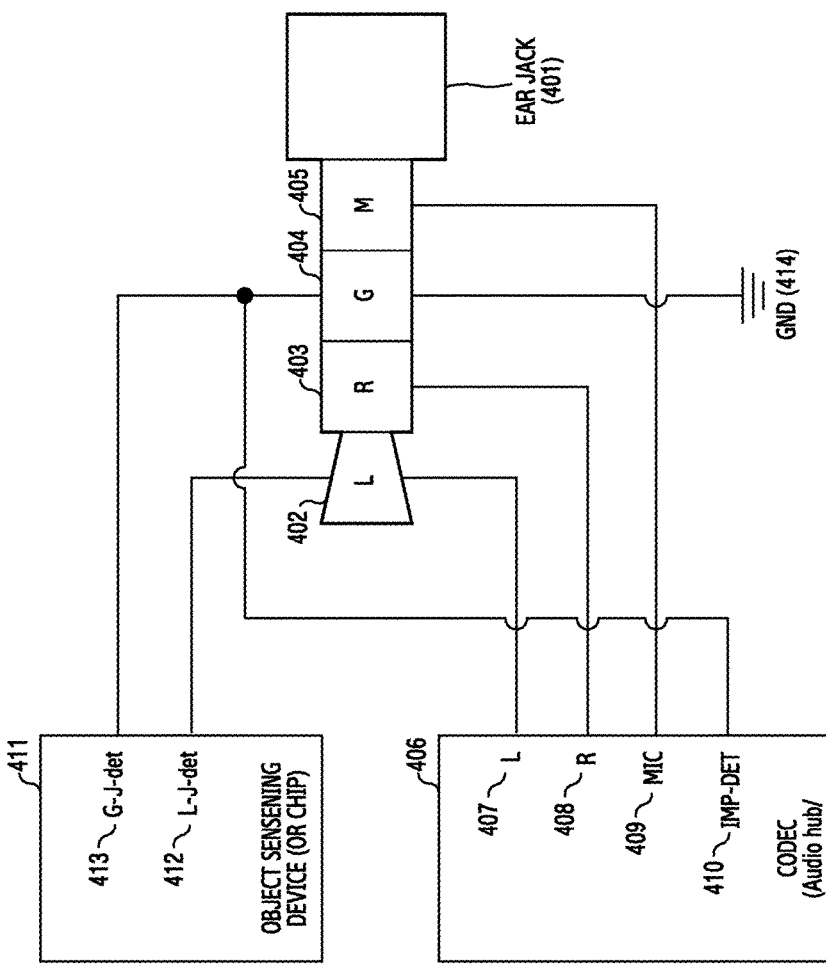
FIG. 4 illustrates a second embodiment of an ear jack according to an embodiment of the present invention.

FIG. 4 illustrates a second embodiment of an ear jack according to the present invention. According to various embodiments, the ear jack 401 provided in an electronic device is connected with an object sensing device (or chip) 411 and a codec 406. According to one embodiment, the object sensing device (or chip) 411 includes a left-terminal jack detector (L-J-Det) 412 and a Ground-terminal jack detector (G-J-Det) 413. According to one embodiment, the codec 406 includes a left (L) side 407, a right (R) side 408, a microphone (MIC) side 409, and an impedance detector (IMP-Det) 410. According to one embodiment, the codec 406 may be an audio hub/audio driving chip. According to one embodiment, a central processing unit (i.e., an application processor or chip) (not shown) may be connected with the object sensing device 411 and the codec 406, to control a general operation of the electronic device.

According to various embodiments, the ear jack 401 includes a left (L) terminal 402, a right (R) terminal 403, a ground (G) terminal 404, and a microphone (M) terminal 405. According to one embodiment, one side of the L terminal 402 connects with the left (L) side 407 of the codec 406. The left (L) side 407 of the codec 406 outputs sound signals generated in the electronic device. The other side of the L terminal 402 connects with the left-terminal jack detector (L-J-Det) 412. The left-terminal jack detector (L-J-Det) 412 detects if an object such as an earplug or moisture is in the ear jack 401. According to one embodiment, the L terminal 402 may output sound signals, outputted from the L side 407 of the codec 406, in the direction of the earplug, when the earplug is inserted into the ear jack 401.

According to various embodiments, the R terminal 403 connects with a right (R) side 408 of the codec 406. The right (R) side 408 of the codec 406 outputs sound signals generated in the electronic device. According to one embodiment, the R terminal 403 outputs sounds from the R side 408 of the codec 406, in the direction of the earplug, when the earplug is inserted into the ear jack 401.

According to various embodiments, one side of the G terminal 404 connects with the ground 414. The other side of the G terminal 404 connects with a Ground-terminal jack detector (G-J-Det) 413 and an impedance detector (IMP-DET) 410. The Ground-terminal jack detector (G-J-Det) 413 detects if an object is in the ear jack 401. The impedance detector (IMP-DET) 410 determines the impedance of the G terminal 404 when it is determined that the object in the ear jack 401 is the earplug.

According to various embodiments, the M terminal 405 connects with a microphone (MIC) side 409 of the codec 406. The microphone (MIC) side 409 of the codec 406 receives an input of sound signals when the earplug is inserted into the ear jack 401.

According to various embodiments, the L side 407 of the codec 406 may output sound signals generated in the electronic device to the L terminal 402. According to one embodiment, the L side 407 of the codec 406 receives a set predetermined electric current at a predetermined interval from the L-terminal jack detector (L-J-Det) 412.

According to various embodiments, the R side 408 of the codec 406 outputs sound signals generated in the electronic device to the R terminal 403.

According to various embodiments, the MIC side 409 of the codec 406 connects with the M terminal 405, and receives an input of sound signals from the earplug inserted into the ear jack 401.

According to various embodiments, upon sensing that the object is located at the G terminal 404, the impedance detector (IMP-Det) 410 applies a set predetermined electric current (or voltage) in the direction of the G terminal 404, and determines the impedance of the G terminal 404.

According to various embodiments, the L-terminal jack detector (L-J-Det) 412 applies a set electric current in the direction of the L terminal 402, and detects if an object is at the L terminal 402. According to one embodiment, by applying a set predetermined electric current at a predetermined interval in the direction of the L terminal 402 and sensing a variation of the impedance of the L terminal 402, the left-terminal jack detector (L-J-Det) 412 determines if the object such as the earplug or moisture is located at the L terminal 402.

According to various embodiments, the Ground-terminal jack detector (G-J-Det) 413 applies a set electric current in the direction of the G terminal 404, and detects if the object is sensed at the G terminal 404. According to one embodiment, by applying a set predetermined electric current at a predetermined interval in the direction of the G terminal 404 and sensing a variation of the impedance of the G terminal 404, the Ground-terminal jack detector (G-J-Det) 413 determines if the object such as the earplug or moisture is located at the G terminal 404.

According to various embodiments, the ground (G) 414 receives a set predetermined electric current from the Ground-terminal jack detector (G-J-Det) 413 and the impedance detector (IMP-Det) 410. According to one embodiment, the ground (G) 414 receives a set predetermined electric current from the Ground-terminal jack detector (G-J-Det) 413. According to one embodiment, the ground (G) 414 receives a set predetermined electric current from the impedance detector (IMP-Det) 410.

Figure 5:
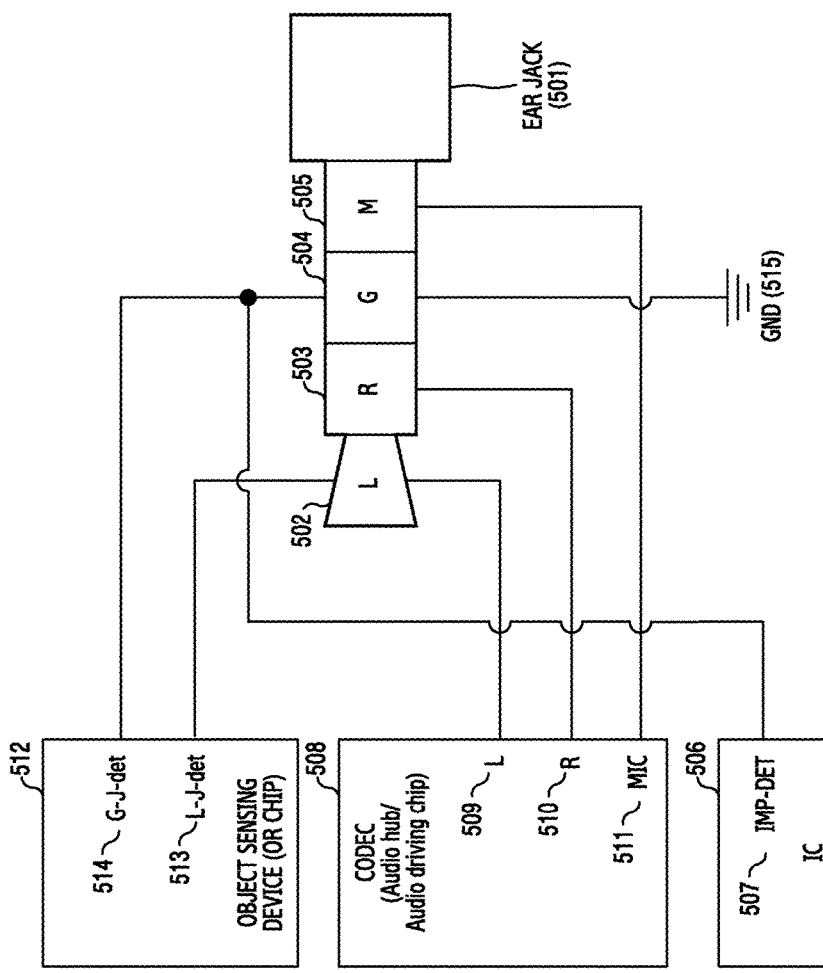
FIG. 5 illustrates a third embodiment of an ear jack according to an embodiment of the present invention.

FIG. 5 illustrates a third embodiment of an ear jack according to the present invention. According to various embodiments, the ear jack 501 provided in an electronic device connects with an object sensing device (or chip) 512, a codec 508, and an integrated circuit (IC) 506. According to one embodiment, the object sensing device (or chip) 512 includes a left-terminal jack detector (L-J-Det) 513 and a Ground-terminal jack detector (G-J-Det) 514. According to one embodiment, the codec 508 includes a left (L) side 509, a right (R) side 510, and a microphone (MIC) side 511, and the IC 506 includes an impedance detector (IMP-Det) 507. That is, the impedance detector (IMP-Det) 507 is included in the IC 506 as a separate constituent element, instead of being included in the codec 508. According to one embodiment, the codec 508 is an audio hub/audio driving chip. According to one embodiment, a central processing unit (i.e., an application processor) (not shown) is connected with the object sensing device (or chip) 512 and the codec 508, and controls a general operation of the electronic device.

According to various embodiments, the ear jack 501 includes a left (L) terminal 502, a right (R) terminal 503, a ground (G) terminal 504, and a microphone (M) terminal 505. According to one embodiment, one side of the L terminal 502 connects with a left (L) side 509 of the codec 508. The left (L) side 509 of the codec 508 outputs sound signals generated in the electronic device. The other side of the L terminal 502 connects with a left-terminal jack detector (L-J-Det) 513. The left-terminal jack detector (L-J-Det) 513 detects if an object such as an earplug or moisture is in the ear jack 501. According to one embodiment, the L terminal 502 outputs sound signals, outputted from the L side 509 of the codec 508, in the direction of the earplug, when the earplug is inserted into the ear jack 501.

According to various embodiments, the R terminal 503 connects with a right (R) side 510 of the codec 508. The right (R) side 510 of the codec 508 outputs sound signals generated in the electronic device. According to one embodiment, the R terminal 503 may output sound signals, outputted from the R side 510 of the codec 508, in the direction of the earplug, when the earplug is inserted into the ear jack 501.

According to various embodiments, one side of the G terminal 504 connects with the ground 515. The other side of the G terminal 504 connects with a Ground-terminal jack detector (G-J-Det) 514 and an impedance detector (IMP-DET) 507. The Ground-terminal jack detector (G-J-Det) 514 detects if an object is in the ear jack 501. The impedance detector (IMP-DET) 507 determines the impedance of the G terminal 504 when it is determined that the object sensed in the ear jack 501 is the earplug.

According to various embodiments, the M terminal 505 connects with a microphone (MIC) side 511 of the codec 508. The microphone (MIC) side 511 of the codec 508 receives an input of sound signals from the earplug inserted into the ear jack 501.

According to various embodiments, the L side 509 of the codec 508 may output sound signals generated in the electronic device, to the L terminal 502. According to one embodiment, the L side 509 of the codec 508 receives a set predetermined electric current at a predetermined interval from the L-terminal jack detector (L-J-Det) 513.

According to various embodiments, the R side 510 of the codec 508 outputs sound signals generated in the electronic device, to the R terminal 503.

According to various embodiments, the MIC side 511 of the codec 508 connects with the M terminal 505, and receives an input of sound signals from the earplug inserted into the ear jack 501.

According to various embodiments, upon sensing that the object is located at the G terminal 504, the impedance detector (IMP-Det) 507 applies a set predetermined electric current (or voltage) in the direction of the G terminal 504, and determines the impedance of the G terminal 504.

According to various embodiments, the L-terminal jack detector (L-J-Det) 513 applies a set electric current in the direction of the L terminal 502, and detects if an object is sensed at the L terminal 502. According to one embodiment, by applying a set predetermined electric current at a predetermined interval in the direction of the L terminal 502 and sensing a variation of the impedance of the L terminal 502, the left-terminal jack detector (L-J-Det) 513 determines if the object such as the earplug or moisture is located at the L terminal 502.

According to various embodiments, the Ground-terminal jack detector (G-J-Det) 514 applies a set electric current in the direction of the G terminal 504, and detects if the object is at the G terminal 504. According to one embodiment, by applying a set predetermined electric current at a predetermined interval in the direction of the G terminal 504 and sensing a variation of the impedance of the G terminal 504, the Ground-terminal jack detector (G-J-Det) 514 determines if the object such as the earplug or moisture is located at the G terminal 504.

According to various embodiments, the ground (G) 515 receives a set predetermined electric current from one or both of the Ground-terminal jack detector (G-J-Det) 514 and the impedance detector (IMP-Det) 507.

According to various embodiments, an electronic device may include an object sensor for determining if an object is detected at a first terminal and a second terminal among terminals of an ear jack, an impedance detector for, if the object is detected, determining the impedance of the second terminal, and a processor for determining whether the object is an earplug in accordance with whether a value of the determined impedance is greater than or equal to a set value.

According to one embodiment, the plurality of terminals are provided that include a Left (L) terminal, a Right (R) terminal, a Ground (G) terminal, and a Microphone (M) terminal.

According to one embodiment, the first terminal is the L terminal, and the second terminal is the G terminal.

According to one embodiment, one side of the first terminal is connected to a coder/decoder (codec), and the other side of the first terminal is connected to the object sensor.

According to one embodiment, one side of the second terminal is connected to the impedance detector and the object sensor, and the other side of the second terminal is connected to the ground.

According to one embodiment, the object sensor is connected to each of the one side of each of the first terminal and the second terminal, to detect the object.

According to one embodiment, the impedance detector applies a set electric current or voltage to the second terminal and the ground, to determine the impedance of the second terminal.

According to one embodiment, if the value of the determined impedance is greater than or equal to a set value, the processor determines that moisture has been introduced into the ear jack.

According to one embodiment, if a set time lapses, the impedance detector determines the impedance of the second terminal.

According to one embodiment, if the determined impedance value is less than the set value, the processor determines that the earplug has been inserted into the ear jack.

Figure 6B:
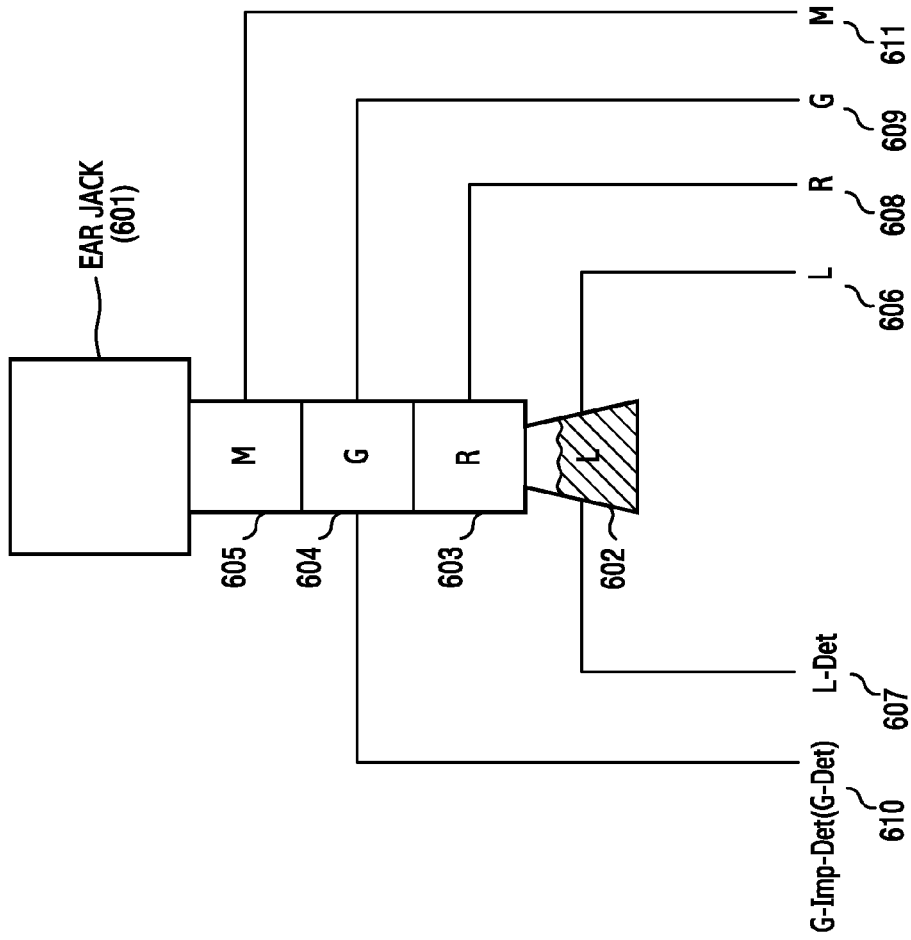
FIGS. 6A and 6B illustrate an embodiment of an electronic device when an object is sensed at an ear jack according to an embodiment of the present invention.
Figure 6A:
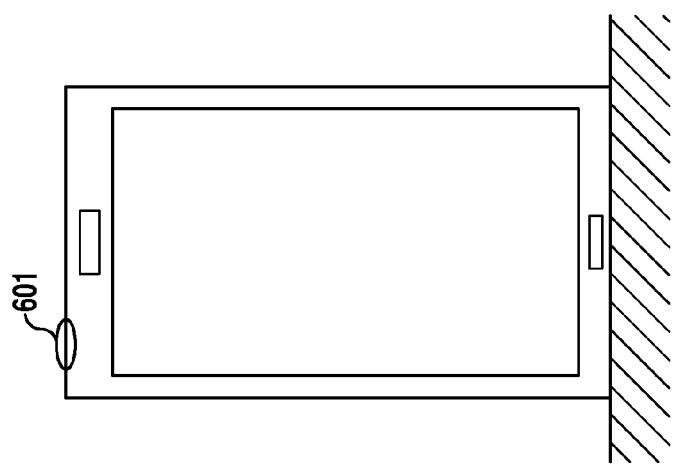

FIGS. 6A and 6B illustrate an embodiment of an electronic device when an object is sensed at an ear jack according to the present invention. According to various embodiments, a plurality of terminals is provided in the ear jack of the electronic device. For example, as illustrated in FIGS. 6A and 6B, the plurality of terminals provided in the ear jack 601 of the electronic device are a left (L) terminal 602, a right (R) terminal 603, a ground (G) terminal 604, and a microphone (M) terminal 605. In FIGS. 6A and 6B, ear jack 601 is elevated in relation to the electronic device.

According to various embodiments, one side of the L terminal 602 connects with a left (L) side 606. The left (L) side 606 outputs sound signals generated in the electronic device. The other side of the L terminal 602 connects with a left-terminal detector (L-Det) 607. The left-terminal detector (L-Det) 607 detects if an object such as an earplug or moisture is in the ear jack 601. According to one embodiment, the L terminal 602 outputs sound signals, outputted from the L side 606, in the direction of the earplug, when the earplug is inserted into the ear jack 601.

According to various embodiments, the R terminal 603 connects with a right (R) side 608. The right (R) side 608 outputs sound signals generated in the electronic device. According to one embodiment, the R terminal 603 outputs sound signals from the R side 608, in the direction of the earplug, when the earplug is inserted into the ear jack 601.

According to various embodiments, one side of the G terminal 604 connects with the ground 609. The other side of the G terminal 604 connects with a G-terminal impedance detector/G-terminal jack detector (G-imp-Det/G-Det) 610. The G-terminal impedance detector/G-terminal jack detector (G-imp-Det/G-Det) 610 detects if an object is in the ear jack 601, and determines the impedance of the G terminal 604 when it is determined that the object sensed in the ear jack 601 is the earplug. According to various embodiments, the M terminal 605 connects with the M (MIC) side 611. The M (MIC) side 611 receives an input of sound signals from the earplug inserted into the ear jack 601. Below, a description is provided for an embodiment when the ear jack 601 of the electronic device heads in the up direction from the ground, as illustrated in FIGS. 6A and 6B, a circuit is operated depending on whether the object sensed in the ear jack 601.

As shown in FIGS. 6A and 6B, the L-terminal detector (L-Det) 607 provided in the ear jack 601 of the electronic device applies a set electric current in the direction of the L terminal 602, and detects if an object is at the L terminal 602. According to one embodiment, by applying a set predetermined electric current at a predetermined interval in the direction of the L terminal 602 and sensing a variation of the impedance of the L terminal 602, the left-terminal detector (L-Det) 607 determines if the object is located at the L terminal 602.

In the aforementioned example, the left-terminal detector (L-Det) 607 provided in the ear jack 601 of the electronic device checks that the change of impedance of the L terminal 602 is sensed, as a result of applying the set predetermined electric current at a predetermined interval in the direction of the L terminal 602.

According to various embodiments, the G-terminal impedance detector/G-terminal jack detector (G-imp-Det/G-Det) 610 detects if the object such as the earplug or moisture is in the G terminal 604. According to one embodiment, by applying a set predetermined electric current at a predetermined interval in the direction of the G terminal 604 and sensing a variation of the impedance of the G terminal 604, the G-terminal impedance detector/G-terminal jack detector (G-imp-Det/G-Det) 610 determines if the object is located at the G terminal 604.

In the aforementioned example, the G-terminal impedance detector/G-terminal jack detector (G-imp-Det/G-Det) 610 provided in the ear jack 601 of the electronic device checks for a change of impedance of the G terminal 604, as a result of applying the set predetermined electric current at a predetermined interval in the direction of the G terminal 604.

According to various embodiments, the electronic device according to the present invention may not determine the impedance of the G terminal 604 of the ear jack 601, since the electronic device according to the present invention does not operate until the object is concurrently detected at the L terminal 602 and the G terminal 604. Accordingly, the electronic device determines that the earplug has not been inserted into the ear jack 601, and does not convert into an earphone mode.

FIGS. 7A and 7B illustrate another embodiment of an electronic device when an object is sensed at an ear jack according to the present invention. According to various embodiments, a plurality of terminals is provided in the ear jack of the electronic device. For example, as illustrated in FIGS. 7A and 7B, the plurality of terminals provided in the ear jack 701 of the electronic device may be a left (L) terminal 702, a right (R) terminal 703, a ground (G) terminal 704, and a microphone (M) terminal 705. In FIGS. 7A and 7B, ear jack 701 is on a same level as the electronic device.

According to various embodiments, one side of the L terminal 702 connects with a left (L) side 706. The left (L) side 706 outputs sound signals generated in the electronic device. The other side of the L terminal 702 connects with a left-terminal detector (L-Det) 707. The left-terminal detector (L-Det) 707 detects if an object such as an earplug or moisture is in the ear jack 701. According to one embodiment, the L terminal 702 outputs sound signals, outputted from the L side 706, in the direction of the earplug, when the earplug is inserted into the ear jack 701.

According to various embodiments, the R terminal 703 connects with a right (R) side 708. The right (R) side 708 outputs sound signals generated in the electronic device. According to one embodiment, the R terminal 703 outputs sound signals, outputted from the R side 708, in the direction of the earplug, when the earplug is inserted into the ear jack 701.

According to various embodiments, one side of the G terminal 704 connects with the ground 709. The other side of the G terminal 704 connects with a G-terminal impedance detector/G-terminal jack detector (G-imp-Det/G-Det) 710. The G-terminal impedance detector/G-terminal jack detector (G-imp-Det/G-Det) 710 detects if an object is in the ear jack 701, and determines the impedance of the G terminal 704 when it is determined that the object sensed in the ear jack 701 is the earplug.

According to various embodiments, the M terminal 705 connects with the M (MIC) side 711. The M (MIC) side 711 receives an input of sound from the earplug inserted into the ear jack 701. Below, a description is made for an embodiment in which, when the ear jack 701 of the electronic device is horizontal or is maintained at an angle less than 90 degrees with the ground, as illustrated in FIGS. 7A and 7B, a circuit is operated depending on the object sensed in the ear jack 701.

According to various embodiments, the L-terminal detector (L-Det) 707 provided in the ear jack 701 of the electronic device applies a set electric current in the direction of the L terminal 702, and detects if an object is at the L terminal 702. According to one embodiment, by applying a set predetermined electric current at a predetermined interval in the direction of the L terminal 702 and sensing a variation of the impedance of the L terminal 702, the left-terminal detector (L-Det) 707 determines if the object is located at the L terminal 702.

In the aforementioned example, the left-terminal detector (L-Det) 707 provided in the ear jack 701 of the electronic device senses a change of impedance of the L terminal 702, since moisture has been introduced into the L terminal 702 as a result of applying the set predetermined electric current at a predetermined interval in the direction of the L terminal 702.

According to various embodiments, the G-terminal impedance detector/G-terminal jack detector (G-imp-Det/G-Det) 710 detects that the object at the G terminal 704 is moisture by applying a set predetermined electric current at a predetermined interval in the direction of the G terminal 704 and sensing a variation of the impedance of the G terminal 704.

In the aforementioned example, the G-terminal impedance detector/G-terminal jack detector (G-imp-Det/G-Det) 710 provided in the ear jack 701 of the electronic device senses that the change of impedance of the G terminal 704, since moisture has been introduced into the G terminal 704 as a result of applying the set predetermined electric current at a predetermined interval in the direction of the G terminal 704.

According to various embodiments, if the electronic device determines that an object is detected at the L terminal 702 and the G terminal 704 among terminals of the ear jack, the G-terminal impedance detector/G-terminal jack detector (G-imp-Det/G-Det) 710 applies a set predetermined electric current (or voltage) in the direction of the G terminal 704 and the ground 709, and determines the impedance of the G terminal 704. For example, when the electric current applied in the direction of the G terminal 704 and the ground 709 in the G-terminal impedance detector/G-terminal jack detector (G-imp-Det/G-Det) 710 is 1 Ampere (A), and the voltage detected in the G terminal 704 is 20 Kilo Volt (KV), the G-terminal impedance detector/G-terminal jack detector (G-imp-Det/G-Det) 710 may determine an impedance value of the G terminal 704 as 20 KΩ.

According to various embodiments, the electronic device determines whether the sensed object is the earplug depending on whether a value of impedance determined in the G-terminal impedance detector/G-terminal jack detector (G-imp-Det/G-Det) 710 is greater than or equal to a set value. According to one embodiment, if it is determined that the value of the impedance determined in the G-terminal impedance detector/G-terminal jack detector (G-imp-Det/G-Det) 710 is greater than or equal to the set value, the electronic device may determine that moisture, not the earplug, has been introduced into the ear jack 701. For example, when the impedance value being set in the electronic device is 20 KΩ, in the aforementioned example, the electronic device may determine that moisture, not the earplug, has been introduced into the ear jack 701, because the impedance value of the G terminal 704 is determined as 20 KΩ. Accordingly, the electronic device may determine that the earplug has not been inserted into the ear jack 701, and not convert into an earphone mode.

FIG. 8 illustrates a further embodiment of an electronic device when an object is sensed at an ear jack according to the present invention. According to various embodiments, a plurality of terminals is provided in the ear jack of the electronic device. For example, as illustrated in FIG. 8, the plurality of terminals provided in the ear jack 801 of the electronic device include a left (L) terminal 802, a right (R) terminal 803, a ground (G) terminal 804, and a microphone (M) terminal 805.

According to various embodiments, one side of the L terminal 802 connects with a left (L) side 806. The left (L) side 806 outputs sound signals generated in the electronic device. The other side of the L terminal 802 connects with a left-terminal detector (L-Det) 807. The left-terminal detector (L-Det) 807 detects if an object such as an earplug 812 or moisture is in the ear jack 801. According to one embodiment, the L terminal 802 outputs sound signals, outputted from the L side 806, in the direction of the earplug 812, when the earplug 812 is inserted into the ear jack 801.

According to various embodiments, the R terminal 803 connects with a right (R) side 808. The right (R) side 808 outputs sound signals generated in the electronic device. According to one embodiment, the R terminal 803 outputs sound signals outputted from the R side 808, in the direction of the earplug 812, when the earplug 812 is inserted into the ear jack 801.

According to various embodiments, one side of the G terminal 804 connects with the ground 809. The other side of the G terminal 804 connects with a G-terminal impedance detector/G-terminal jack detector (G-imp-Det/G-Det) 810. The G-terminal impedance detector/G-terminal jack detector (G-imp-Det/G-Det) 810 detects if an object is in the ear jack 801, and determines the impedance of the G terminal 804 when it is determined that the object sensed in the ear jack 801 is the earplug 812.

According to various embodiments, the M terminal 805 connects with the M (MIC) side 811. The M (MIC) side 811 may receive an input of sound signals from the earplug 812 inserted into the ear jack 801. Below, a description is made for an embodiment in which, when the earplug 812 is inserted into the ear jack 801 of the electronic device as illustrated in FIG. 8, a circuit is operated depending on the object sensed in the ear jack 801.

According to various embodiments, the L-terminal detector (L-Det) 807 provided in the ear jack 801 of the electronic device applies a set electric current in the direction of the L terminal 802, and detects if an object is at the L terminal 802. According to one embodiment, by applying a set predetermined electric current at a predetermined interval in the direction of the L terminal 802 and sensing a variation of the impedance of the L terminal 802, the left-terminal detector (L-Det) 807 determines if the object is located at the L terminal 802.

In the aforementioned example, the left-terminal detector (L-Det) 807 provided in the ear jack 801 of the electronic device senses the change of impedance of the L terminal 802, since the earplug 812 is located at the L terminal 802 as a result of applying the set predetermined electric current at a predetermined interval in the direction of the L terminal 802.

According to various embodiments, the G-terminal impedance detector/G-terminal jack detector (G-imp-Det/G-Det) 810 detects if the object such as the earplug 812 or moisture is sensed at the G terminal 804. According to one embodiment, by applying a set predetermined electric current at a predetermined interval in the direction of the G terminal 804 and sensing a variation of the impedance of the G terminal 804, the G-terminal impedance detector/G-terminal jack detector (G-imp-Det/G-Det) 810 determines if the object is located at the G terminal 804.

In the aforementioned example, the G-terminal impedance detector/G-terminal jack detector (G-imp-Det/G-Det) 810 provided in the ear jack 801 of the electronic device senses the change of impedance of the G terminal 804, since the earplug 812 is located at the G terminal 804 as a result of applying the set predetermined electric current at a predetermined interval in the direction of the G terminal 804.

According to various embodiments, if the electronic device determines that an object is detected at the L terminal 802 and the G terminal 804 among terminals of the ear jack, the G-terminal impedance detector/G-terminal jack detector (G-imp-Det/G-Det) 810 applies a set predetermined electric current (or voltage) in the direction of the G terminal 804 and the ground 809, and determines the impedance of the G terminal 804. For example, when the electric current applied in the direction of the G terminal 804 and the ground 809 in the G-terminal impedance detector/G-terminal jack detector (G-imp-Det/G-Det) 810 is 1 Ampere (A), and the voltage detected in the G terminal 804 is 500 V, the G-terminal impedance detector/G-terminal jack detector (G-imp-Det/G-Det) 810 may determine an impedance value of the G terminal 804 as 500Ω.

According to various embodiments, the electronic device determines whether the sensed object is the earplug 812 depending on whether a value of impedance determined in the G-terminal impedance detector/G-terminal jack detector (G-imp-Det/G-Det) 810 is greater than or equal to a set value. According to one embodiment, if it is determined that the value of the impedance determined in the G-terminal impedance detector/G-terminal jack detector (G-imp-Det/G-Det) 810 is less than the set value, the electronic device determines that the earplug 812 has been introduced into the ear jack 801. For example, when the impedance value being set in the electronic device is 20 KΩ, in the aforementioned example, the electronic device may determine that the earplug 812 has been introduced into the ear jack 801, because the impedance value of the G terminal 804 is determined as 500Ω. Accordingly, the electronic device may check that the earplug 812 has been inserted into the ear jack 801, thus converting into an earphone mode.

Figure 9:
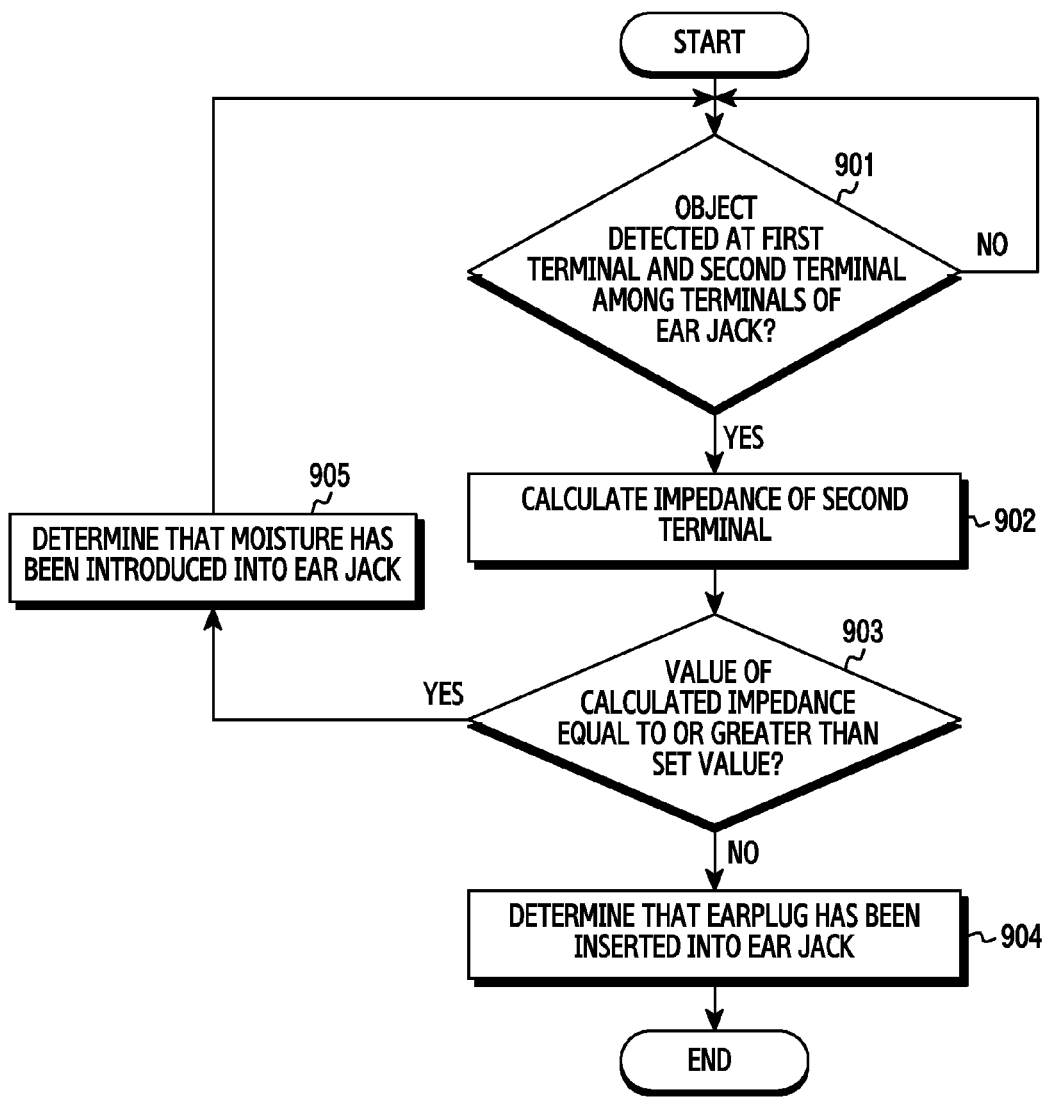
FIG. 9 is a flowchart of an operation of an electronic device according to an embodiment of the present invention.

FIG. 9 is a flowchart of an operation of an electronic device according to the present invention.

In step 901 of FIG., the electronic device determines if an object is detected at a first terminal and a second terminal among terminals of an ear jack.

If in step 901 the electronic device determines that the object is detected at the first terminal and the second terminal among the terminals of the ear jack, in step 902, the electronic device calculates the impedance of the second terminal. As described above, the G-terminal impedance detector (G-imp-Det) of the electronic device applies a set predetermined electric current (or voltage) in the direction of the G terminal and the ground, and determines the impedance of the G terminal.

In step 903, the electronic device determines if the calculated impedance value is greater than or equal to a set value. For example, as described above, when the impedance value being set in the electronic device is set as 20 KΩ, the electronic device determines whether the calculated impedance value of the G terminal is greater than or equal to 20 KΩ.

If in step 903 it is determined that the impedance value calculated in the electronic device is less than the set value, the electronic device determines in step 904 that an earplug has been inserted into the ear jack. For example, as described above, when the electronic device determines that the impedance value of the G terminal is equal to 500Ω, the electronic device determines that the earplug has been inserted into the ear jack.

If in step 901 the electronic device determines that the object is not detected at the first terminal and the second terminal among the terminals of the ear jack, the electronic device returns to step 901.

If in step 903 it is determined that the impedance value calculated in the electronic device is greater than or equal to the set value, the electronic device determines that moisture has been introduced into the ear jack. As described above, when the impedance value in the electronic device is set as 20 KΩ, and the calculated impedance value of the G terminal is determined as 50 KΩ, the electronic device determines that moisture has been introduced into the ear jack, and the electronic device returns to step 901. The electronic device may repeat the aforementioned step 901, since moisture in the ear jack of the electronic device may evaporate.

Figure 10:
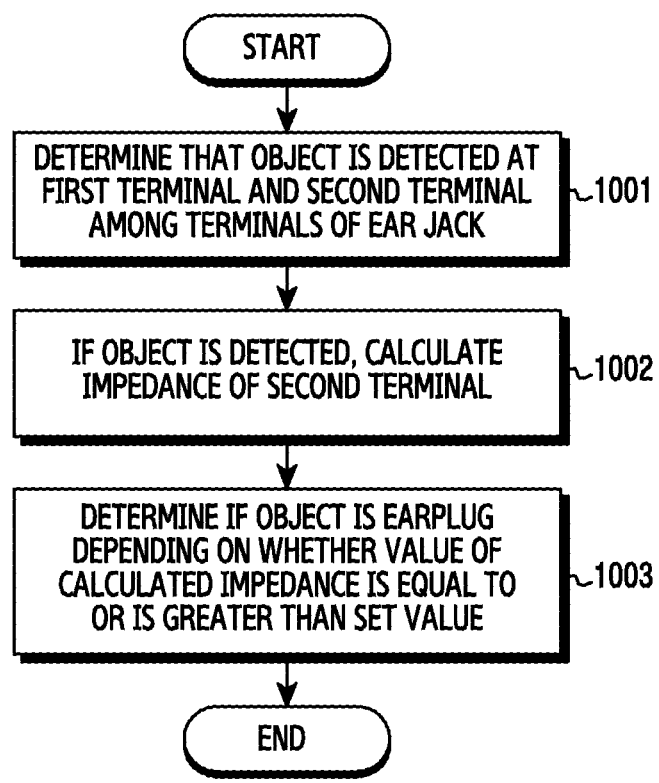
FIG. 10 is a flowchart of a method of an electronic device according to an embodiment of the present invention.

FIG. 10 is a flowchart of a method of an electronic device according to the present invention.

In step 1001 of FIG. 10, the electronic device detects an object at a first terminal and a second terminal among terminals of an ear jack.

If the object is detected, the electronic device determines the impedance of the second terminal in step 1002. As described above, the G-terminal impedance detector (G-imp-Det) of the electronic device applies a set predetermined electric current (or voltage) in the direction of the G terminal and the ground, and calculates the impedance of the G terminal.

In step 1003, the electronic device determines whether the object is an earplug depending on whether a value of the calculated impedance is greater than or equal to a set value.

According to various embodiments, a method of operation an electronic device is provided that includes determining if an object is detected at a first terminal and a second terminal among terminals of an ear jack, if the object is detected, calculating the impedance of the second terminal, and determining if the object is an earplug in accordance with whether a value of the determined impedance is greater than or equal to a set value.

According to one embodiment, determining if the object is detected includes detecting the object in the object sensor connected to each of the one sides of the first terminal and the second terminal.

According to one embodiment, determining the impedance of the second terminal includes checking that a set electric current or voltage is applied to the second terminal from the impedance detector and is introduced to the ground, and determining the impedance of the second terminal in the impedance detector.

According to one embodiment, determining if the object is the earplug includes, if the value of the determined impedance is greater than or equal to a set value, determining that moisture is introduced into the ear jack.

According to one embodiment, if a set time lapses, the impedance of the second terminal is determined.

According to one embodiment, determining if the object is the earplug includes, if the determined impedance value is less than the set value, determining that the earplug has been inserted into the ear jack.

Various embodiments of the present invention provide an apparatus and method capable of, when an object is sensed at a first terminal of an ear jack and a second terminal thereof, determining the impedance of the second terminal and determining whether an earplug is inserted into the ear jack, thereby being able to prevent a malfunction of the ear jack caused by the introduction of moisture.

Embodiments of the present invention disclosed in the present specification and drawings merely suggest specific examples so as to easily describe the technological content of the present invention and help the understanding of the present invention, and are not intended to limit the spirit and scope of the present invention. Accordingly, it should be understood that the scope of the present invention includes all modifications or changes drawn on the basis of the technological spirit of the present invention besides the embodiments disclosed herein, as defined by the appended claims and their equivalents.

What is claimed is:

1. A method of operation of an electronic device, the method comprising:
    detecting a change of a first impedance of a first terminal among a plurality of terminals of an ear jack and a change of a second impedance of a ground terminal among the plurality of terminals of the ear jack;
    determining that an object is detected at both the first terminal and the ground terminal based on the detection;
    in response to determining that the object is detected at both the first terminal and the ground terminal, calculating the impedance of the ground terminal;
    determining whether the object is moisture according to the calculated second impedance of the ground terminal in a state in which the object is detected at both the first terminal and the ground terminal; and
    in response to determining that the object is moisture, using a path other than a path associated with the ear jack when outputting an audio signal.

2. The method of claim 1, wherein the plurality of terminals comprise a left terminal, a right terminal, the ground terminal, and a microphone terminal.

3. The method of claim 1, wherein the first terminal comprises a left terminal.

4. The method of claim 1, wherein one side of the first terminal is connected with a coder/decoder, and the other side of the first terminal is connected with an object sensor.

5. The method of claim 3, wherein one side of the ground terminal is connected with an impedance detector and an object sensor, and the other side of the ground terminal is connected to ground.

6. The method of claim 1, wherein determining that the object is detected comprises detecting the object by an object sensor connected to each of the first terminal and the ground terminal.

7. The method of claim 1, wherein calculating the second impedance of the ground terminal comprises:
    checking that a set electric current or voltage is applied to the ground terminal from an impedance detector and is introduced to ground; and
    calculating, by the impedance detector, the second impedance of the ground terminal.

8. The method of claim 1, wherein determining whether the object is the moisture comprises, determining that the moisture is in the ear jack in response to the calculated second impedance being greater than or equal to a set value.

9. The method of claim 8, further comprising, recalculating the second impedance of the ground terminal after a lapse of a set time.

10. The method of claim 8, wherein determining whether the object is the moisture comprises determining that an earplug is in the ear jack in response to the calculated second impedance value being less than the set value.

11. An electronic device comprising:
    an object sensor configured to detect a change of a first impedance of a first terminal among a plurality of terminals of an ear jack and a change of a second impedance of a ground terminal among the plurality of terminals of the ear jack, and determine that an object is detected at both the first terminal and the ground terminal based on the detection;
    an impedance detector configured to calculate, in response to determining that the object is detected at both the first terminal and the ground terminal, the second impedance of the ground terminal; and
    a processor configured to determine whether the object is moisture according to the calculated second impedance of the ground terminal in a state in which the object is detected at both the first terminal and the ground terminal, and in response to determining that the object is moisture, using a path other than a path associated with the ear jack when outputting an audio signal.

12. The device of claim 11, wherein the plurality of terminals include a left terminal, a right terminal, the ground terminal, and a microphone terminal.

13. The device of claim 11, wherein the first terminal comprises a left terminal.

14. The device of claim 11, wherein one side of the first terminal is connected with a coder/decoder, and the other side of the first terminal is connected with the object sensor.

15. The device of claim 13, wherein one side of the ground terminal is connected with the impedance detector and the object sensor, and the other side of the ground terminal is connected to ground.

16. The device of claim 11, wherein the object sensor is connected to each of the first terminal and the ground terminal, and is configured to detect the object.

17. The device of claim 11, wherein the impedance detector is configured to apply a set electric current or voltage to the ground terminal and to ground, and calculate the second impedance of the ground terminal.

18. The device of claim 11, wherein, the processor is configured to determine that the moisture is in the ear jack, in response to the calculated second impedance being greater than or equal to a set value.

19. The device of claim 18, wherein the impedance detector is configured to recalculate the second impedance of the ground terminal after a lapse of a set time.

20. The device of claim 18, wherein the processor is configured to determine that an earplug is in the ear jack, in response to the calculated second impedance being less than the set value.

* * * * *